| United States Patent [19] | [11] Patent Number: 4,465,852 |
| Sato | [45] Date of Patent: Aug. 14, 1984 |

[54] PROCESS FOR THE PRODUCTION OF CARBOXYLIC ACID ESTERS

[75] Inventor: Haruhito Sato, Sodegaura, Japan

[73] Assignee: Idemitsu Kosan Company Limited, Tokyo, Japan

[21] Appl. No.: 330,010

[22] Filed: Dec. 11, 1981

[30] Foreign Application Priority Data

Dec. 25, 1980 [JP] Japan .................. 55-182856

[51] Int. Cl.³ .............................................. C07C 67/04
[52] U.S. Cl. ...................... 560/247; 260/410.9 R; 560/180; 560/190; 560/205; 560/226
[58] Field of Search ............... 560/247, 205, 226, 190, 560/180; 260/410.9 R

[56] References Cited

U.S. PATENT DOCUMENTS

| 3,076,840 | 2/1963 | Brandenburg | 560/247 |
| 3,085,108 | 4/1963 | Stepanek | 560/247 |
| 3,096,365 | 7/1963 | Heisler | 560/247 |
| 3,492,341 | 1/1970 | Trevillyan | 560/247 |
| 4,365,084 | 12/1982 | Young | 560/247 |

OTHER PUBLICATIONS

Rabo, "Zeolite Chemistry and Catalysis" (ACS Monograph 171), pp. 615–618, (1976).

*Primary Examiner*—Michael L. Shippen
*Attorney, Agent, or Firm*—Frishauf, Holtz, Goodman & Woodward

[57] ABSTRACT

A process for producing carboxylic acid esters by reacting an olefin and a carboxylic acid in the presence of a crystalline metallosilicate catalyst. The catalyst has a mole ratio of silica to metal oxide of at least 12. The metal of the metal oxide is an element selected from the group consisting of the elements belonging to Groups III, IV, V, VI B, and VIII of the Periodic Table. The catalyst is preferably zeolitic, for example zeolitic aluminosilicate. The process is particularly effective when reacting relatively inactive olefins such as methylene and propylene.

14 Claims, No Drawings

PROCESS FOR THE PRODUCTION OF CARBOXYLIC ACID ESTERS

BACKGROUND OF THE INVENTION

The present invention relates to a process for the production of carboxylic acid esters by reacting olefins with carboxylic acids. It is known that the reaction of olefins and carboxylic acids results in the formation of the corresponding carboxylic acid esters. This reaction is usually performed in the presence of liquid catalysts, e.g., (1) strong acid catalysts, such as sulfuric acid and a combination of boron trifluoride ($BF_3$) and hydrogen fluoride (HF), and (2) media containing the free heteropolyacid of phosphomolybdic acid or phosphotungstic acid, and water.

The catalysts listed in (1) above, however, have the serious defect that they cause corrosion of apparatus. The catalysts listed in (2) above also have disadvantages. They produce alcohols together with the desired carboxylic acid esters. When ethylene is used as a starting material, the ethyl ester cannot be prepared since it is usually converted into a sec-butylester. The conventional methods using the aforedescribed catalysts are disadvantageous in that because the catalysts are liquid, the methods require specific equipment for the separation of products from the catalysts, and for purification of products, etc.

In order to remove the above disadvantages, a method using various ion exchange resins has been proposed. This method suffers from disadvantages in that it is not possible to increase the temperature and pressure to higher levels in order to increase the yield, because the ion exchange resin catalysts are seriously deteriorated by heat, and in that the reproduction of the catalyst is difficult.

It has also been proposed to use Y-type zeolite and mordenite zeolite as solid acid catalysts. These zeolite catalysts, however, have the defect that when reacting ethylene and propylene, the rate of reaction is very small although it is observed that they exhibit high reactivity to isobutylene. In the production of carboxylic acid esters by the use of the zeolite catalysts, it is known that the reactivity is determined by the number of carbon atoms and structure of the olefin used. The influence of the carboxylic acid on the reactivity is small. It is, therefore, apparent that when the olefin used is isotubylene, the reaction proceeds easily, whereas when the olefin used is, in particular, ethylene, the reaction proceeds with difficulty since the reaction of an olefin with a carboxylic acid becomes more difficult as the number of carbon atoms of the olefin is decreased.

SUMMARY OF THE INVENTION

As a result of extensive investigations to develop a process for efficiently producing various carboxylic acid esters by reacting olefins with carboxylic acids even when the olefins have a small number of carbon atoms, such as ethylene and propylene which are of low reactivity, in particular the production of acetic acid esters, etc., which are widely used as solvents, it has now been found that cryatalline metallosilicates having a specific crystal structure exhibit very high catalytic activity and are thermally stable, and that since the crystalline metallosilicates are in solid form, they are readily handled during processing.

The present invention provides a process for the production of carboxylic acid esters which comprises reacting olefins and carboxylic acids in the presence of crystalline metallosilicates wherein the molar ratio of silica to metal oxide is at least 12, and the metal constituting the metal oxide is selected from the elements belonging to Groups III, IV, V, VI B and VIII of the Periodic Table.

DETAILED DESCRIPTION OF THE INVENTION

In the crystalline metallosilicate used as the catalyst, the molar ratio of silica to metal oxide is at least 12, i.e., it is very rich in silica content.

The crystalline metallosilicate used in the present invention is explained in detail with reference to crystalline aluminosilicate zeolite in which the metal oxide is alumina ($Al_2O_3$), which is believed to be particularly useful.

The crystalline aluminosilicate zeolite is a crystal in which $SiO_4$ and $AlO_4$ tetrahedrons, each containing the silicon (Si) or aluminum (Al) atom at the center and the four oxygen atoms at the variations thereof, are bound together in a three-dimensional net structure while sharing the oxygen atoms at the vertices. It has a skeletal structure in which cages of various sizes are regularly piled on one another. An example of such crystalline aluminosilicate zeolite is ZSM-5-Zeolite (produced by Mobil Oil Co.) in which silicon and aluminum atoms are bound together through oxygen atoms in a ring-like form, each ring containing ten oxygen atoms, and which has pores of 6 to 7 Å.

In the crystalline metallosilicate used in the present invention, metal of the metal oxide is not present in the form of cation or precipitate, but is present as a metal atom component of the crystal frame structure (e.g., the tetrahedral structure). The crystalline metallosilicate has similar catalytic action irrespective of the type of metal of the metal oxide since it has always the same crystal structure as for aluminum, i.e., the above described structure of aluminosilicate zeolite even when the metal is any of the elements belonging to Groups III, IV, V, VI B and VIII of the Periodic Table. This is clearly supported by X-ray analytical results as shown in Tables 1, 2 and 3 of crystalline aluminosilicate zeolite and other metal-containing crystalline zeolites, and it is furthermore apparent from the fact that crystalline zeolite consisting of silica alone (Silicalite produced by Union Carbide Corp.) has the same crystal structure as above.

The metal of the metal oxide may be any of the elements belonging to Groups III, IV, V, VI B and VIII of the Periodic Table, including boron, phosphorus, etc. which are not usually considered to be metals. Preferred examples include platinum, antimony, boron, aluminum, indium, arsenic, yttrium, zirconium, vanadium, chromium, molybdenum, iron, ruthenium, palladium, and gallium. In addition, germanium, tin, phosphorus, bismuth, lanthanum, titanium, tungsten, cobalt, nickel, rhodium, iridium, and osmium can be used.

The molar ratio of silica to metal oxide in the crystalline metallosilicate is, as described above, at least 12, and the maximum molar ratio is about 10,000. When the molar ratios are less than 12, the catalyst is not desirable in that the absorption onto carboxylic acids is high and the heat resistance is low. Usually, therefore, it is preferred that the molar ratio is 15 or more. But in the case of the above described Silicalite which does not contain any metal oxide, such as alumina, the reaction almost does not proceed, and the objects of the invention cannot be attained. The ratio of silica to the metal oxide is more preferably at least about 20. It is preferably between about 20 and 500.

Silica, an alkali metal, a compound of a metal belonging to Group III, IV, V, VI B or VIII of the Periodic Table (the compound is not always necessarily an oxide), and water are mixed. The mixture is reacted at a temperature of 80° to 300° C. and preferably 120° to 200° C. for a period of 0.5 hour to 30 days and preferably 5 hours to 10 days in the presence of a crystalline metallosilicate seed crystal and/or tetraalkylammonium ions, alkylamines, aminoalcohols, morpholine, etc.

The H-type crystalline metallosilicate is prepared by partially exchanging alkali metal ion or alkaline earth metal ion in the crystalline silicate with ammonium ion and then calcining the obtained silicate or ion-exchanging it with hydrochloric acid.

The thus prepared zeolite may be mixed with a carrier and formed into granules and, thereafter, activated by calcining at a temperature of 300° to 700° C.

In producing the above crystalline metallosilicate, if desired, two or more metal compounds may be used although it is usual to use one metal compound. When one metal compound is used, the crystalline zeolite had the three-dimensional net structure of $SiO_4$ in which some of the silicon atoms are replaced by the other metal atoms. When two or more metal compounds are used, the crystalline zeolite has a three-dimensional net structure in which some of the silicon atoms are replaced by atoms of the two or more metals. Of the crystalline metallosilicates as used herein, a crystalline metallosilicate in which some of the silicon atoms are replaced by aluminum (Al), i.e., crystalline aluminosilicate zeolite is preferred.

In accordance with the process of the invention, olefins and carboxylic acids are reacted in the presence of the above prepared crystalline metallosilicate catalyst to produce the corresponding carboxylic acid esters. Examples of olefins which can be used in the invention include ethylene, propylene, butylene, isobutylene, 2-ethyl-2-pentene, 2-propyl-2-butene, 2-methyl-2-pentene, 2-isopropyl-2-butene, 1-butene, 2-butene, 2-pentene, 2-hexene, 3-methyl-1-butene, 2-methyl-1-butene, 2,4,4-trimethyl-1-butene, 2-ethyl-1-pentene, 2-methyl-1-pentene, 2-propyl-1-butene, 2-isopropyl-1-butene, and 2-methyl-2-hexene. Preferably the olefin containing up to about 8 carbon atoms. The process of the invention is particularly useful for producing the corresponding carboxylic acid esters from ethylene or propylene.

The carboxylic acids used in the present invention may be monocarboxylic acids, or dicarboxylic acids containing two carboxylic acid groups. The number of carbon atoms in the carboxylic acids is not limited, but is preferably from 1 to 16. These carboxylic acids may be substituted by a halogen atom, a hydroxyl group, a nitro group, an amino group, a sulfonic acid group, a carbonyl group, an alkyl group, or an alkoxyl group. Examples of carboxylic acids which can be used in the invention include formic acid, acetic acid, propionic acid, butylic acid, isobutylic acid, valeric acid, 2,2-dimethylpropionic acid, caproic acid, acrylic acid, methacrylic acid, crotonic acid, chloroacetic acid, adipic acid, succinic acid, palmitic acid, stearic acid, oleic acid, oxalic acid, and malic acid.

The reaction of olefins and carboxylic acids in the presence of the crystalline metallosilicate catalyst can be performed, batchwise or continuously, by various known methods. From a practical standpoint, the continuous method in which a feed mixture of olefin and carboxylic acid is continuously introduced into a reactor packed with the catalyst and the ester product is continuously withdrawn therefrom, is advantageous over the batch method. In addition, the reaction may be performed in the gas phase or liquid phase.

The reaction temperature is not critical, and it is usually from 100° C. to 300° C. and preferably from 150° C. to 250° C. The reaction pressure is also not critical, and it is usually from atmospheric pressure to high pressures and preferably from 5 atmospheres to 200 atmospheres. There are no special limitations to the ratio of olefin to carboxylic acid being fed. They are usually fed at a molar ratio of olefin to carboxylic acid of 1 or more.

The following examples and comparative examples are given to illustrate the invention in greater detail although the invention is not limited thereto.

EXAMPLES 1 TO 6 AND COMPARATIVE EXAMPLES 1 TO 4

(1) Preparation of Catalyst

Eighty parts by weight of each Catalysts A to G, which were prepared as described hereinbelow or commercially available, and 20 parts by weight of alumina sol (calculated as solids) were kneaded and formed into granules, and then calcined at 500° C. for 6 hours to prepare an experimental catalyst.

Catalyst A

A mixture of 7.52 grams of aluminum sulfate (18 hydrate) and 17.6 grams of sulfuric acid (97%) was dissolved in 250 milliliters of water to prepare a solution (Solution A). Also, a solution of 162 grams of water glass in 300 milliliters of water (Solution B) and a solution of 79 grams of sodium chloride in 122 milliliters of water (Solution C) were prepared. Solutions A and B were gradually added dropwise to Solution C while stirring. Then, 1 gram of crystalline aluminosilicate zeolite (which had been prepared by adding 25 grams of brominated tetrapropylammonium as an organic compound to the same mixture of Solutions A, B and C as above and reacting the resulting mixture in the same manner as described hereinafter) was added to the mixture of Solutions A, B and C. The resulting mixture was then adjusted to pH 10.0, placed in a one-liter autoclave, and reacted at 170° C. under the self-pressure for 20 hours while stirring at a number of rotation of 200 r.p.m.

The reaction mixture was cooled and washed five times with 1 liter of water. Thereafter, solids were separated by filtration and dried at 120° C. for 3 hours to obtain 40.5 grams of crystalline aluminosilicate zeolite. This crystalline aluminosilicate zeolite contained some crystalline sodium silicate. The results of X-ray diffraction analysis of the crystalline aluminosilicate zeolite are shown in Table 1.

The composition (molar ratio) of the zeolite was as folllows:

$Na_2O:SiO_2:Al_2O_3 = 0.9:60:1.0$

B.E.T. surface area of the zeolite was 330 square meters per gram.

Forty grams of the thus prepared zeolite is calcined at 500° C. for 6 hours and steeped in 200 milliliters of 1 Normal ammonium nitrate solution ($NH_4NO_3$) and stirred for 24 hours. Thereafter, the solid zeolite is separated by filtration and washed with 2 liters of distilled water and dried at 120° C. for 4 hours and then calcined at 550° C. for 6 hours.

TABLE 1

| Distance between Lattice Planes (Å) | Relative Intensity | Distance between Lattice Planes (Å) | Relative Intensity | Distance between Lattice Planes (Å) | Relative Intensity |
|---|---|---|---|---|---|
| 11.32 | strong | 5.18 | weak | 3.75 | strong |
| 10.16 | strong | 5.03 | weak | 3.66 | weak |
| 7.46 | weak | 4.95 | weak | 3.46 | weak |
| 6.41 | weak | 4.78 | weak | 3.32 | weak |
| 6.06 | weak | 4.39 | weak | 3.16 | weak |
| 5.96 | weak | 4.29 | weak | 3.05 | weak |
| 5.75 | weak | 4.10 | weak | 2.99 | weak |
| 5.64 | weak | 3.88 | very strong | | |

Catalyst B

A solution consisting of 3.2 grams of boron oxide, 12.2 grams of monoethanolamine, 17.6 grams of sulfuric acid (97%), and 250 milliliters of water was prepared (Solution A). Also, a solution of 162 grams of water glass (SiO$_2$: 37.6% by weight; Na$_2$O: 17.5% by weight; water: 44.9% by weight) in 300 milliliters of water (Solution B), and a solution of 79 grams of sodium chloride in 122 milliliters of water (Solution C) were prepared. Solutions A and B were gradually added dropwise to Solution C at the same time at room temperature while stirring. The mixture was placed in a one-liter autoclave, and reacted at 170° C. under the self-pressure for 20 hours while stirring at a number of rotation of 200 r.p.m.

The reaction mixture was cooled and washed five times with 1 liter of water. Thereafter, solids were separated by filtration and dried at 120° C. for 3 hours to obtain 53 grams of crystalline zeolite. The results of X-ray diffraction analysis of the crystalline zeolite are shown in Table 2.

The composition (molar ratio) of the crystalline zeolite was as follows:

Na$_2$O:SiO$_2$:B$_2$O$_3$ = 1.7:118:2

B.E.T. surface area of the zeolite was 327 square meters per gram.

Forty grams of the thus prepared zeolite is calcined at 500° C. for 6 hours and steeped in 200 milliliters of 1 Normal ammonium nitrate solution (NH$_4$NO$_3$) and stirred for 24 hours. Thereafter, the solid zeolite is separated by filtration and washed with 2 liters of distilled water and dried at 120° C. for 4 hours and then calcined at 550° C. for 6 hours.

TABLE 2

| Distance between Lattice Planes (Å) | Relative Intensity | Distance between Lattice Planes (Å) | Relative Intensity | Distance between Lattice Planes (Å) | Relative Intensity |
|---|---|---|---|---|---|
| 11.23 | strong | 5.73 | weak | 3.72 | strong |
| 10.07 | strong | 5.58 | weak | 3.65 | strong |
| 9.81 | weak | 5.01 | weaK | 3.48 | weak |
| 7.47 | weak | 4.61 | weak | 3.44 | weak |
| 7.10 | weak | 4.37 | weak | 3.33 | weak |
| 6.73 | weak | 4.27 | weak | 3.31 | weak |
| 6.38 | weak | 4.01 | weak | 3.05 | weak |
| 6.06 | weak | 3.85 | very strong | 2.98 | weak |
| 6.01 | weak | 3.75 | strong | 2.95 | weak |

Catalyst C

A crystalline zeolite was prepared in the same manner as in the preparation of Catalyst B except that chromium oxide was used in place of boron oxide. B.E.T. surface area of the zeolite was 273 square meters per gram.

Catalyst D

A solution consisting of 4.0 grams of boron oxide, 7.52 grams of aluminum sulfate (18 hydrate), 8.7 grams of morpholine, 17.6 grams of sulfuric acid (97%), and 250 milliliters of water was prepared (Solution A). Also, a solution of 162 grams of water glass (SiO$_2$:37.6% by weight; Na$_2$O: 17.5% by weight; water: 44.9% by weight) in 300 milliliters of water (Solution B), and a solution of 79 grams of sodium chloride in 122 milliliters of water (Solution C) were prepared. Solutions A and B were gradually added dropwise to Solution C at the same time at room temperature while stirring. The mixture was placed in a one-liter autoclave, and reacted at 170° C. under the self-pressure for 20 hours while stirring at the number of rotation of 200 r.p.m.

The reaction mixture was cooled and washed five times with 1 liter of water. Thereafter, solids were separated by filtration and dried at 120° C. for 3 hours to obtain 53.5 grams of crystalline aluminosilicate zeolite. The results of X-ray diffraction analysis of the crystalline aluminosilicate zeolite are shown in Table 3.

The composition (molar ratio) of the crystalline aluminosilicate zeolite was as follows:

Na$_2$O:SiO$_2$:Al$_2$O$_3$:B$_2$O$_3$ = 1.5:118:1:5

B.E.T. surface are of the zeolite was 320 square meters per gram.

Forty grams of the thus prepared zeolite is calcined at 500° C. for 6 hours and steeped in 200 milliliters of 1 Normal ammonium nitrate solution (NH$_4$NO$_3$) and stirred for 24 hours. Thereafter, the solid zeolite is separated by filtration and washed with 2 liters of distilled water and dried at 120° C. for 4 hours and then calcined at 550° C. for 6 hours.

TABLE 3

| Distance between Lattice Planes (Å) | Relative Intensity | Distance between Lattice Planes (Å) | Relative Intensity | Distance between Lattice Planes (Å) | Relative Intensity |
|---|---|---|---|---|---|
| 11.47 | strong | 4.67 | weak | 3.46 | weak |
| 10.27 | strong | 4.41 | weak | 3.37 | weak |
| 6.45 | weak | 4.31 | weak | 3.35 | weak |
| 6.10 | weak | 3.88 | very strong | 3.08 | weak |
| 5.79 | weak | 3.75 | strong | 3.01 | weak |
| 5.64 | weak | 3.69 | strong | 2.97 | weak |

Catalyst E
H-mordenite
Catalyst F
Lanthanum-exchanged Y-type zeolite
Catalyst G
Silicalite (crystalline silicate) (prepared in accordance with the method disclosed in Japanese Patent Application Laid-Open No. 75499/1979).

(2) Reaction Experiment

The crystalline metal silicate catalyst was placed in a tubular flow type high pressure reactor having an inner diameter of 20 millimeters, and additionally, 30 milliliters of quartz sand was charged thereto. The food was introduced into the reactor from the top thereof, and the reaction was performed under the conditions shown in Table 4. The reaction products were withdrawn from the bottom of the reactor, and were subjected to gas-liquid separation. The concentration by weight of ester in the liquid was measured, and the results are shown in Table 4.

TABLE 4

| | Example 1 | Comparative Example 1 | Comparative Example 2 | Example 2 | Example 3 | Example 4 | Comparative Example 3 | Example 5 | Comparative Example 4 |
|---|---|---|---|---|---|---|---|---|---|
| Catalyst | A | F | G | B | C | D | E | D | F |
| Amount of Catalyst (milliliters) | 20 | 20 | 20 | 6 | 6 | 6 | 6 | 6 | 6 |
| Olefin | ethylene | ethylene | ethylene | propylene | propylene | ethylene | ethylene | propylene | propylene |
| Feed Rate of Olefin (liters per minute at 20° C. | 1.0 | 1.0 | 1.0 | 0.5 | 0.5 | 1.0 | 1.0 | 0.5 | 0.5 |
| Carboxylic Acid | acetic acid | acetic acid | acetic acid | acetic acid | acetic acid | acetic acid | acetic acid | acetic acid | acetic acid |
| Feed Rate of Carboxylic Acid (grams per hour) | 20 | 20 | 20 | 10 | 10 | 20 | 20 | 10 | 10 |
| Reaction Temperature (°C.) | 200 | 200 | 200 | 160 | 160 | 200 | 200 | 160 | 160 |
| Reaction Pressure (kilograms per square centimeter) | 20 | 20 | 20 | 6 | 6 | 20 | 20 | 6 | 6 |
| Concentration of Ethyl Acetate or Isopropyl Acetate in Reaction Solution (% by weight) | | | | | | | | | |
| After 1 hour | 30 | 3 | 0.8 | 5.4 | 3.2 | 5.4 | 0.8 | 11.0 | 0 |
| After 2 hours | 50 | 0 | 0.2 | 5.7 | 3.6 | 7.7 | 0.2 | 10.2 | 0 |
| After 4 hours | 40 | 0 | 0 | 5.2 | 3.7 | 8.7 | 0 | 7.3 | 0 |
| After 6 hours | 32 | 0 | 0 | 5.2 | 3.7 | 9.1 | 0 | 6.4 | 0 |

I claim:

1. A process for producing a carboxylic acid ester comprising reacting an olefin selected from the group consisting of ethylene, propylene and butylene with a carboxylic acid selected from the group consisting of formic acid, acetic acid, propionic acid, butylic acid, isobutylic acid, valeric acid, 2,2-dimethylpropionic acid, caproic acid, acrylic acid, methacrylic acid, crotonic acid, chloroacetic acid, adipic acid, succinic acid, palmitic acid, stearic acid, oleic acid, oxalic acid, and malic acid, in the presence of a crystalline silicate having a molar ratio of silica to oxide of at least 12, said oxide being selected from the group consisting of boron oxide, chromium oxide and a combination of boron oxide and aluminum oxide, and wherein said crystalline silicate is prepared in the presence of at least one of (i) a nitrogen containing substance selected from the group consisting of tetraalkylammonium ion, alkylamine, aminoalcohol, and morpholine, and (ii) a crystalline silicate seed crystal prepared in the presence of said nitrogen containing substance.

2. The process of claim 1, wherein said olefin is selected from the group consisting of ethylene and propylene.

3. The process of claim 1, wherein said crystalline silicate is a zeolite metal silicate.

4. The process of claim 2, wherein said crystalline silicate is a zeolitic metal silicate.

5. The process of claim 1, wherein said crystalline silicate also contains an alkali oxide.

6. The process of claim 1, wherein said crystalline silicate is supported on a carrier.

7. The process of claim 1, wherein said reaction is carried out at a temperature from about 100° C. to 300° C. and at a pressure of up to 200 atmospheres.

8. The process of claim 7, wherein said carboxylic acid is acetic acid.

9. The process of claim 5, wherein said zeolitic metal silicate also contains sodium oxide.

10. The process of claim 6 or 8, wherein said carrier is alumina.

11. The process of claim 1, 5 or 6, wherein said molar ratio of silica to oxide is at least about 20.

12. The process of claim 1, 4, or 8, wherein said molar ratio of silica to oxide is between about 20 and 500.

13. The process of claim 1, wherein said olefin is selected from the group consisting of ethylene and propylene, said carboxylic acid is acetic acid, and the reaction is conducted at a temperature between 160° C. and 200° C. at a pressure of between 6 and 20 kg/cm$^2$.

14. The process of claim 13, wherein said crystalline silicate is supported on alumina.

* * * * *